United States Patent
Takeuchi

[19]

[11] Patent Number: 5,807,260
[45] Date of Patent: Sep. 15, 1998

[54] ULTRASOUND IMAGING METHODS AND APPARATUS

[75] Inventor: Yasuhito Takeuchi, Tokyo, Japan

[73] Assignee: GE Yokogawa Medical Systems, Limited, Tokyo, Japan

[21] Appl. No.: 872,552

[22] Filed: Jun. 12, 1997

[30] Foreign Application Priority Data

Jul. 18, 1996 [JP] Japan .................................. 8-189283

[51] Int. Cl.⁶ .................................................. A61B 8/00
[52] U.S. Cl. .................................................. 600/462
[58] Field of Search ........................ 600/462, 463, 600/442, 443

[56] References Cited

U.S. PATENT DOCUMENTS

| | | | |
|---|---|---|---|
| 4,936,307 | 6/1990 | Saito et al. ............................. | 600/463 |
| 5,257,629 | 11/1993 | Kitney et al. .......................... | 600/463 |
| 5,373,849 | 12/1994 | Maroney et al. ....................... | 600/463 |
| 5,435,314 | 7/1995 | Dias ....................................... | 600/463 |

*Primary Examiner*—Marvin M. Lateef
*Assistant Examiner*—Martin Patel
*Attorney, Agent, or Firm*—Moonray Kojima

[57] ABSTRACT

The present invention comprises: a search unit; a hollow guide for stabbing a subject; a manipulating device for protruding the search unit out of the tip of the guide and for moving the search unit along a predetermined orbit; device for transmitting/receiving the ultrasound during the movement by the manipulating means along the orbit; and device for producing an image based on the received echo signal by means of an aperture synthesis technique.

8 Claims, 3 Drawing Sheets

ULTRASOUND IMAGING METHODS AND APPARATUS

FIELD OF THE INVENTION

The present invention relates to ultrasound imaging methods and apparatus in which the imaging is performed with an ultrasonic search unit inserted into a subject.

BACKGROUND OF THE INVENTION

In order to perform the ultrasound imaging as near an imaging site deep in a subject as possible, an insertion ultrasonic probe which is inserted into a body cavity is used. The probe is inserted into the body cavity, such as an esophagus, stomach or rectum, to perform the ultrasonic scanning from the interior of the subject.

One example of the ultrasound imaging apparatus of this type is described, for example, in the Japanese Utility Model Application Laid Open No. 6-19708 and known. In this apparatus, an ultrasonic transducer array contained in a hollow cylindrical guide (trocar) is inserted into the body cavity, then the ultrasound transmission and echo reception are repeated moving the transducer array mechanically along a predetermined orbit with the transducer array protruded out of the tip of the trocar, and an image is reconstructed from the received echo signal by means of an aperture synthesis technique.

Still, some imaging sites cannot be approached enough even by inserting the apparatus into the body cavity and cannot be properly imaged by using such an ultrasound imaging apparatus.

SUMMARY OF THE INVENTION

It is therefore an object of the present invention to provide ultrasound imaging methods and apparatus in which the imaging is performed with an ultrasonic search unit inserted into a tissue of a subject.

In a first aspect, the invention provides an ultrasound imaging method comprising the steps of: inserting an ultrasonic search unit into a soft tissue of a subject for transmitting/receiving ultrasound; transmitting/receiving the ultrasound moving said search unit along a predetermined orbit; and producing an image based on the received signal.

In accordance with the invention, by transmitting/receiving the ultrasound moving the search unit and the surrounding tissue together along a predetermined orbit, and by producing an image based on the received signal, the image through an ultrasound transmission/reception aperture formed by the orbit the search unit moves along can be obtained. Tissues located beyond a distance several times the size of the aperture are not moved and an image of the tissues can be obtained. This means that an ultrasound imaging method is implemented in which the imaging is performed with an ultrasonic search unit inserted into a tissue of a subject near the desired site. In this invention, the image is preferably produced by means of the aperture synthesis technique, in that the image can be obtained in high spatial resolution.

In a second aspect, the present invention provides an ultrasound imaging apparatus comprising: a search unit for transmitting/receiving ultrasound; means for inserting said search unit into a soft tissue of a subject; means for moving said search unit along a predetermined orbit; means for transmitting/receiving the ultrasound via said search unit during the movement by said moving means; and means for producing an image based on the received signal obtained by said transmitting/receiving means.

In accordance with the invention, by transmitting/receiving the ultrasound moving the search unit and the surrounding tissue together along a predetermined orbit, and by producing an image based on the received signal, the image through an ultrasound transmission/reception aperture formed by the orbit the search unit moves along can be obtained. Tissues located beyond a distance several times the size of the aperture are not moved and an image of the tissues can be obtained. This means that an ultrasound imaging apparatus is implemented in which the imaging is performed with an ultrasonic search unit inserted into a tissue of a subject near the desired site. In this invention, the image is preferably produced by means of the aperture synthesis technique, in that the image can be obtained in high spatial resolution.

In a third aspect, the present invention provides an ultrasound imaging apparatus comprising: a search unit for transmitting/receiving ultrasound; a guide for containing said search unit and for stabbing a subject; a manipulating means for putting said search unit in and out from the tip of said guide under a stabbed condition and for moving said search unit along a predetermined orbit; means for transmitting/receiving the ultrasound via said search unit during the movement by said manipulating means along said orbit; and means for producing an image based on the received signal obtained by said transmitting/receiving means.

In accordance with the invention, by transmitting/receiving the ultrasound moving the search unit and the surrounding tissue together along a predetermined orbit, and by producing an image by means of the aperture synthesis technique based on the received signal, the image through an ultrasound transmission/reception aperture formed by the orbit the search unit moves along can be obtained. Tissues located beyond a distance several times the size of the aperture are not moved and an image of the tissues can be obtained. This means that an ultrasound imaging apparatus is implemented in which the imaging is performed with an ultrasonic search unit inserted into a tissue of a subject near the desired site. In this invention, the image is preferably produced by means of the aperture synthesis technique, in that the image can be obtained in high spatial resolution.

Further objects and advantages of the present invention will be apparent from the following description of the preferred embodiments of the invention as illustrated in accompanying drawings.

DETAILED DESCRIPTION OF THE INVENTION

Figure 1:
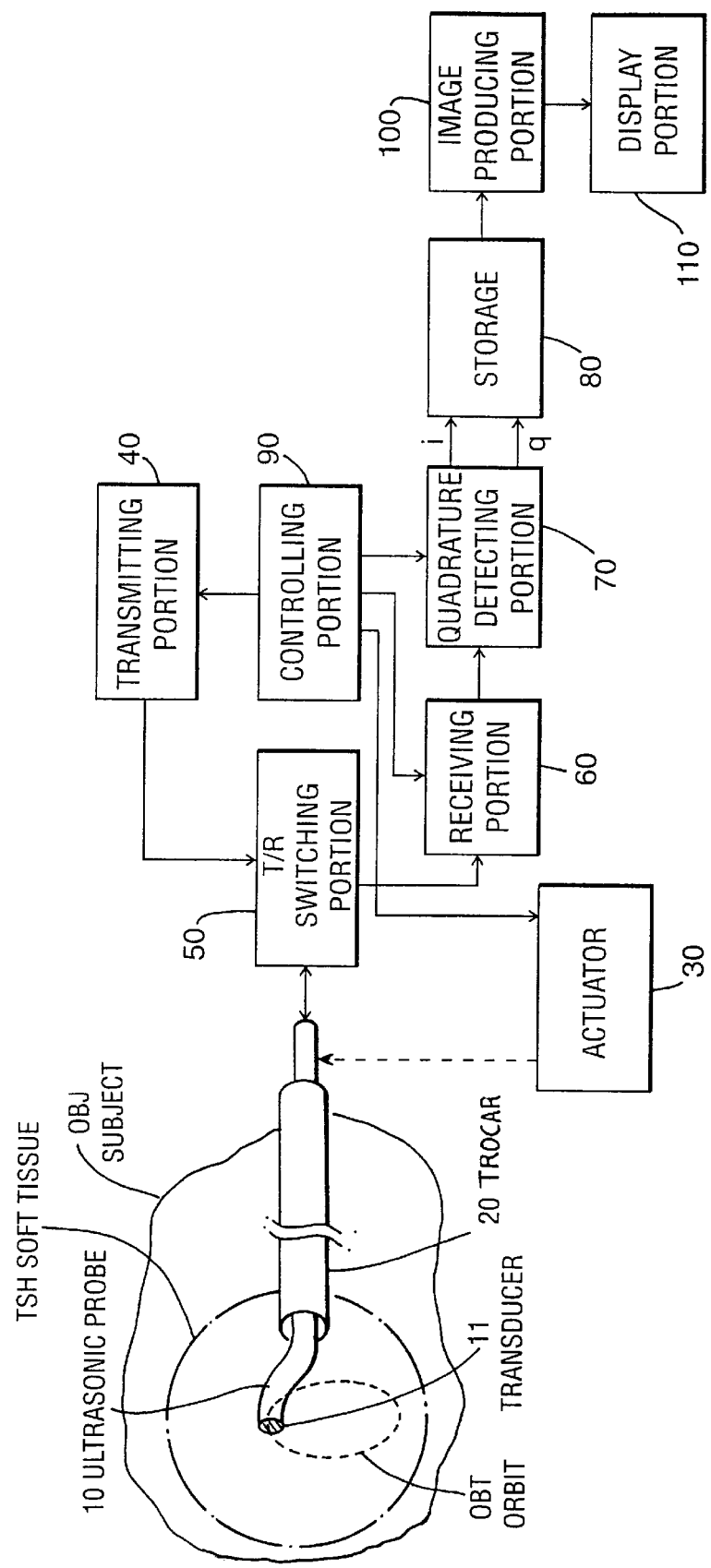
FIG. 1 is a block diagram of an apparatus in accordance with one embodiment of the present invention.

Referring to FIG. 1, there is shown a block diagram of an ultrasound imaging apparatus, which is one embodiment of the present invention. Arrangement of the apparatus represents one embodiment of an apparatus in accordance with the invention, and operation thereof represents one embodiment of a method in accordance with the invention, which similarly applies to other embodiments of the present invention.

As shown in FIG. 1, an ultrasonic probe 10 is inserted into a soft tissue 201 inside a subject or object 200 through a trocar 20. The trocar 20 is a hollow pipe having the stabbing function and the stabbing causes the ultrasonic probe 10 to be inserted into the subject 200.

The ultrasonic probe 10 is drawn into the trocar 20 when being stabbed, and is protruded out of the trocar 20 when the desired site is reached. Alternatively, only the trocar 20 is drawn slightly toward the outside of the subject so that the ultrasonic probe 10 is protruded relative to the trocar 20. As an example, the ultrasonic probe 10 is about 3 mm in diameter, and the trocar 20 is about 5 mm in outer diameter.

The ultrasonic probe 10 has a generally crank-like shape when protruded out of the trocar 20. Since the ultrasonic probe 10 has elasticity, it is straightened when drawn into the trocar 20 and recovers its crank-like shape by elasticity when protruded out thereof.

The ultrasonic probe 10 is provided on its tip surface with an ultrasonic transducer 11. The transducer 11 is, for example, a small disc formed of piezoelectric material. The ultrasonic probe 10 transmits the ultrasound in the direction to which the tip surface is directed, and receives the return echoes which strike the tip surface. The directionality of the ultrasound transmission/reception is predetermined to be sufficiently broad. The central frequency of the ultrasound to be transmitted is predetermined to 20 MHz, for example.

The transducer 11 may be constructed from an array of a plurality of transducer elements rather than from a single-disc transducer, which is preferable in that the directionality of the transmission/reception can be selected as desired by means of a phased array technique. By contrast, the single-disc transducer is preferable in its simple structure.

The ultrasonic probe 10 can be rotated around its portion which is contained in the trocar 20 as a rotation axis. Such a rotation causes the transducer 11 to move along a circular orbit 202. As an example, the circular orbit OBT is about 10 mm in diameter. A surface encompassed within the circular orbit 202 gives an aperture in producing an image by means of the aperture synthesis technique described later, and the aperture is equivalent to that of an annular transducer array which has many transducers along the circular orbit 202, because the ultrasound transmission/reception is sequentially performed by the transducer 11 at the respective positions along the circular orbit 202.

Since the ultrasonic probe 10 is surrounded by the soft tissue 201 and the tissue is also moved together with the ultrasonic probe 10, the probe 10 can be rotated though it is inserted into the tissue. This means that the mechanical scanning is achieved with the ultrasonic probe 10 inserted into the tissue. Only the tissue near the ultrasonic probe 10 is moved and the tissues beyond a certain distance, for example, a distance 3–4 times the diameter of the circular orbit are not moved.

The mechanical scanning by the above-described ultrasonic probe 10 and putting it in and out from the trocar 20 are performed by an actuator 30. The actuator 30 is mechanically connected to the ultrasonic probe 10 and supplies operating parameters for the above-described motion.

A transmitting portion 40 generates a signal for driving the transducer 11 in the ultrasonic probe 10. The driving signal is applied to the transducer 11 through a T/R (transmit/receive) switching portion 50. The ultrasound is thus transmitted from the transducer 11.

The echo of the transmitted ultrasound is received at the transducer 11, and a signal of the echo is supplied to a receiving portion 60 through the T/R switching portion 50. The receiving portion 60 forms a received echo signal at a predetermined level by amplifying the signal of the echo as an RF (radio frequency) signal.

The received echo signal is supplied to and quadrature detected at a quadrature detector 70. The signal is separated into an in-phase component i and a quadrature component q by the quadrature detection. These components i and q are transformed into a digital data sequence at an A/D (analog-to-digital) converter (not shown) and stored in a storage 80. The received echo data is thus stored as complex data in the storage 80. By storing both amplitude and phase information as complex data, a hologram of the echo can be obtained in the storage 80.

A controlling portion 90 supplies control signals to the components ranging from the actuator 30 to the storage 80 and controls the above-described operations, such as the mechanical scanning by the ultrasonic probe 10, the ultrasound transmission/reception, the quadrature detection of the received echo signals and the storage of the hologram. The controlling portion 90 also provides reference signals for the quadrature detection to the quadrature detector 70.

The ultrasound transmission and echo reception are thus performed at the respective positions on the circular orbit OBT of the ultrasonic probe 10 divided into 128 portions, for example, and the complex data representing the received echo signal is stored in the storage 80 each time. The hologram, for example, of the 128 echoes is finished in the storage 80 when the ultrasonic probe 10 completes its circular orbit OBT.

An image producing portion 100 reconstructs an image which represents distribution of the echo reflecting points, i.e., the interior of the subject 200, by means of the aperture synthesis technique using the echo hologram in the storage 80. The image producing portion 100 is one embodiment of image producing means in accordance with the present invention. The image is reconstructed based on the equivalent 2-dimensional aperture 203 (see FIG. 2) encompassed within the circular orbit OBT of the ultrasonic probe 10 by means of the aperture synthesis technique. The scanning orbit of the ultrasonic probe 10 is not limited to a circle but may be any closed orbit as desired. In the latter case, the equivalent 2-dimensional aperture is a surface encompassed within the closed orbit.

The image reconstruction according to the aperture synthesis technique is performed by the convolution of the hologram data and a predetermined kernel.

This is generally represented as:

$$U(x, y, z) = H(x, y, z) * K(x, y, z), \qquad (1)$$

wherein

U: image of the object,

H: hologram, and

K: kernel.

Figure 2:
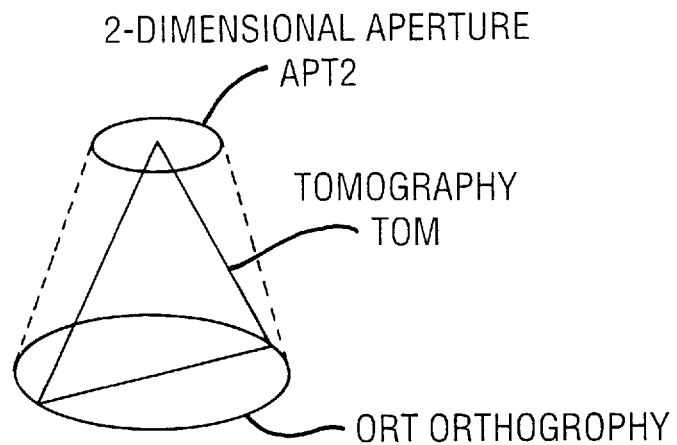
FIG. 2 is a schematic representation illustrating the concept of orthography and tomography along with a 2-dimensional aperture.

In operating the equation (1), omitting z, or the depth, gives orthography, and omitting y, or the height, gives tomography. FIG. 2 illustrates the concept of orthography 205 and tomography 204 along with a 2-dimensional aperture 203.

Reconstructed or produced is the image which represents the region ranging from the tip surface of the ultrasonic probe 10 to the position beyond a distance 3–4 times the diameter of the circular orbit 205, i.e., which represents the portion not moved by the mechanical scanning. The reconstructed image is presented on a display portion 110 as a visual image.

Figure 3:
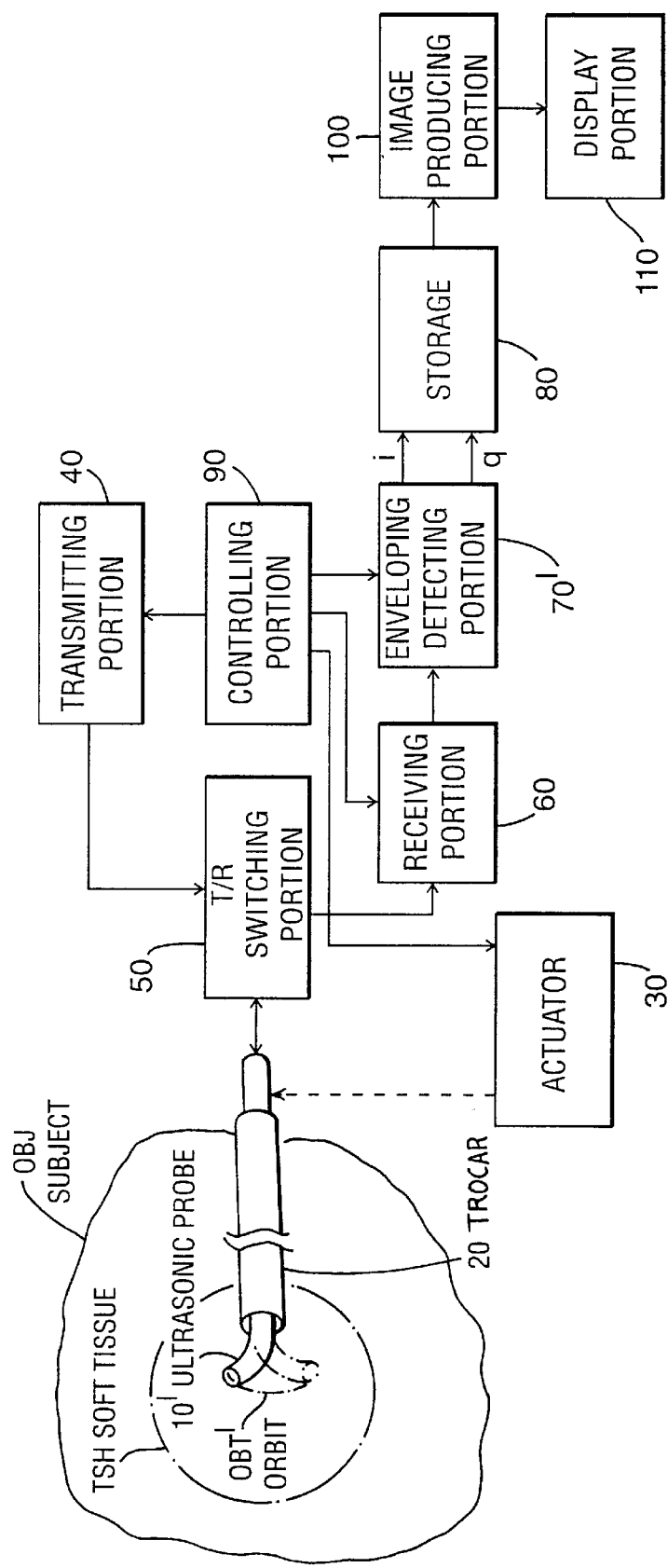
FIG. 3 is a block diagram of an apparatus in accordance with another embodiment of the present invention.

Another embodiment of the present invention is shown in FIG. 3 in which components similar to those illustrated in FIG. 1 are denoted by the same reference numerals and will not be further described. In FIG. 3, the tip of an ultrasonic probe 10' oscillates up and down, for example. The oscillation is manipulated by the actuator 30. The tip surface of the ultrasonic probe 10' is moved along an arc-like orbit 202 as a result of the oscillation. Although the soft tissue 201 near the ultrasonic probe 10' is moved together with the probe 10', the region beyond a distance several times the length of the orbit is not moved. The ultrasound transmission/reception is performed at the respective positions on the arc orbit 202' divided into 64 portions, for example.

The ultrasound is transmitted/received in an ultrasonic beam of narrow directionality. Such an ultrasonic beam is formed by a concave-disc transducer or a phased array. The received echo signal is envelope detected at an envelope detecting portion 70' and stored in the storage 80. A-scope data of the echo is thus stored in the storage 80. A sector region is scanned by one scanning of the ultrasonic probe 10'. The A-scope data of the echo for the sector region, i.e., intensity data of the echo from the respective points on the sound rays in the scanned sector region is stored. The above-described A-scope data is used as 2-dimensional pixel data to produce a tomography of the sector region by the image producing means 100 and the tomography is presented on the display portion 110.

Since such an apparatus produces an image from A-scope data, the image can be obtained much easier than from a hologram by means of the aperture synthesis technique.

Figure 4:
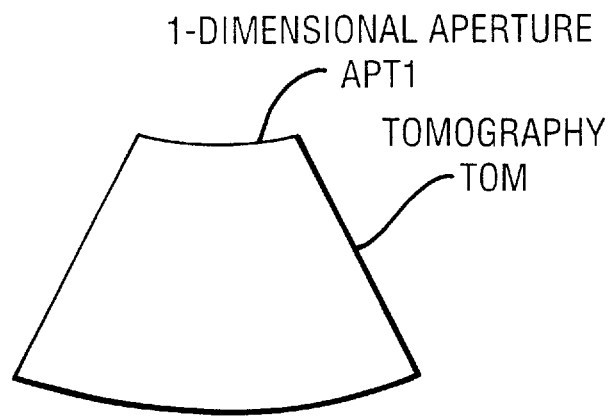
FIG. 4 is a schematic representation illustrating the concept of a 1-dimensional aperture and tomography.

Further, the apparatus shown in FIG. 3 can be used to perform the ultrasound transmission/reception of broad directionality by the ultrasonic probe 10', obtain a hologram by quadrature detecting the received echo signal and, based on the signal, produce an image by means of the aperture synthesis technique, resulting in the image of much higher resolution than that produced from A-scope data. In this case, the equivalent aperture is 1-dimensional. FIG. 4 illustrates the concept of the 1-dimensional aperture 206 and tomography 207.

Many widely different embodiments of the invention may be constructed without departing from the spirit and the scope of the present invention. It should be understood that the present invention is not limited to the specific embodiments described in the specification, except as defined in the appended claims.

What is claimed is:

1. An ultrasonic imaging method utilizing a hollow cylindrical guide and a search unit comprising a crank shaped end movably disposed within said guide and having an ultrasonic transducer, said method comprising the steps of:

inserting said guide and search unit into a soft tissue of a subject;

causing the search unit to project outwardly from the guide and into the soft tissue;

moving the crank-shaped end of said search unit to project outward from the guide and along a predetermined orbit within the soft tissue;

transmitting ultrasonic waves to said transducer of said search unit for transmission to a targeted area of said soft tissue which is a predetermined distance from said orbit so as to not be moved by movement of said search unit;

receiving reflected waves from the targeted area of said soft tissue in said transducer of said search unit; and producing an image of the targeted area of said soft tissue from said reflected waves.

2. The method of claim 1, wherein said moving of said crank shaped end of said search unit is by rotation.

3. The method of claim 1, wherein said moving of said crank shaped end of said search unit is in an up-down motion.

4. The method of claim 1, wherein said image is produced using an aperture synthesis technique.

5. An ultrasonic imaging apparatus comprising:

a hollow cylindrical guide for insertion into a soft tissue of a subject;

a search unit movably disposed within said guide and comprising an ultrasonic transducer, said search unit comprising a flexible crank-shaped end which is retractable into and projected outward from said guide;

means for moving said crank-shaped end of said search unit out of said guide and into said soft tissue and along a predetermined orbit therein;

means for transmitting ultrasonic waves to said search unit transducer for application to a target area of said soft tissue outside of said orbit and for receiving ultrasonic waves reflected from said targeted area of said soft tissue; and means for producing an image from the received ultrasonic waves.

6. The apparatus of claim 5, wherein said means for moving comprises means for rotating said crank-shaped end about an axis of said cylindrical guide.

7. The apparatus of claim 5, wherein said means for moving comprises means for moving said crank-shaped end projected outward from said guide in an up-down direction.

8. The apparatus of claim 5, wherein said image is produced using an aperture synthesis technique.

* * * * *